(12) United States Patent
Farina et al.

(10) Patent No.: US 6,752,967 B2
(45) Date of Patent: Jun. 22, 2004

(54) STACKABLE ALIQUOT VESSEL ARRAY

(75) Inventors: Edward Francis Farina, Oxford, PA (US); Samuel Garfield Ferguson, Jr., Bear, DE (US)

(73) Assignee: Dade Behring Inc., Deerfield, IL (US)

( * ) Notice: Subject to any disclaimer, the term of this patent is extended or adjusted under 35 U.S.C. 154(b) by 331 days.

(21) Appl. No.: 10/037,512

(22) Filed: Jan. 4, 2002

(65) Prior Publication Data

US 2003/0129095 A1 Jul. 10, 2003

(51) Int. Cl.$^7$ ................................................ B01L 3/00
(52) U.S. Cl. .................... 422/102; 422/99; 422/104; 206/509; 206/511; 435/288.4; 435/305.1; 435/305.2; 435/288.3
(58) Field of Search ................. 206/486–490, 206/140, 201, 499, 194, 509, 501, 503–512, 515–565; 422/102, 104, 99; 435/288.4, 288.3, 305.1, 305.2; 211/126.11, 126.12, 189, 194

(56) References Cited

U.S. PATENT DOCUMENTS

| | | |
|---|---|---|
| 938,675 A | 11/1909 | Lorenz |
| D215,431 S | 9/1969 | Allen ........................... D16/1 |
| D226,846 S | 5/1973 | Rosenburg .................... D16/1 |
| 3,912,456 A | 10/1975 | Young ...................... 23/253 R |
| D240,052 S | 5/1976 | Varga ........................ D32/2 C |
| D249,706 S | 9/1978 | Adamski .................... D24/32 |
| 4,178,345 A | 12/1979 | Terk ............................ 422/61 |
| 4,195,060 A | 3/1980 | Terk ............................ 422/61 |
| 4,295,601 A | 10/1981 | Cowell ........................ 233/26 |
| 4,599,314 A | 7/1986 | Shami ........................ 435/287 |
| 4,874,250 A | 10/1989 | Gonner ........................ 374/43 |
| 4,877,659 A | 10/1989 | Vince ........................ 428/34.1 |
| 4,908,320 A | 3/1990 | Zakowski et al. ............ 436/35 |
| 5,077,013 A | 12/1991 | Guigan ........................ 422/64 |
| 5,084,242 A | 1/1992 | Sakuma et al. ............. 422/100 |
| D325,975 S | 5/1992 | Grade et al. ................ D24/230 |
| 5,110,556 A | 5/1992 | Lyman et al. ................ 422/101 |
| 5,424,036 A | 6/1995 | Ushikubo .................... 422/64 |
| 5,622,675 A | 4/1997 | Glenday ..................... 422/102 |
| 5,622,676 A | 4/1997 | Lind .......................... 422/104 |
| 5,642,816 A | 7/1997 | Kelly et al. ................. 211/60.1 |
| 5,679,309 A | 10/1997 | Bell ............................ 422/67 |
| 5,735,387 A | 4/1998 | Polaniec et al. ......... 198/690.1 |
| 5,738,827 A | 4/1998 | Marquiss .................... 422/104 |
| 5,816,406 A | * 10/1998 | Jupille et al. ............... 206/561 |
| 5,849,247 A | 12/1998 | Uzan et al. ................... 422/65 |
| 5,855,847 A | 1/1999 | Oonuma et al. ............. 422/64 |
| 5,885,529 A | 3/1999 | Babson et al. ............... 422/65 |

(List continued on next page.)

*Primary Examiner*—Jill Warden
*Assistant Examiner*—Elizabeth Quan
(74) *Attorney, Agent, or Firm*—Leland K. Jordan

(57) ABSTRACT

An aliquot vessel array having notched side flanges and rails of a next adjacent so that a plurality of arrays may be attached one atop another in a secure stack. Stacked aliquot vessel arrays may be simultaneously loaded into a storage unit on an automatic analyzer and automatically dispensed into a sampling track as required. The aliquot vessel array has certain handling features to ensure safe and reliable movement between the storage unit and sampling tracks.

13 Claims, 10 Drawing Sheets

U.S. PATENT DOCUMENTS

| | | |
|---|---|---|
| 5,897,835 A | 4/1999 | Seaton et al. ................ 422/104 |
| 5,948,363 A | 9/1999 | Gaillard ....................... 422/102 |
| 5,961,925 A | 10/1999 | Ruediger et al. .............. 422/99 |
| 6,027,691 A | 2/2000 | Watts et al. ................... 422/64 |
| 6,060,022 A | 5/2000 | Pang et al. .................... 422/65 |
| 6,086,827 A | 7/2000 | Horner et al. ............... 422/102 |
| 6,098,819 A | 8/2000 | Link ........................ 211/85.13 |
| 6,118,582 A | 9/2000 | Del Bruno .................. 359/398 |
| 6,190,617 B1 | 2/2001 | Clark et al. ................. 422/104 |
| D448,854 S | 10/2001 | Kulper et al. ............... D24/230 |
| D452,740 S | 1/2002 | Brennan et al. ........... D24/226 |
| D461,554 S | 8/2002 | Lafond et al. ................ D24/30 |
| 6,447,726 B1 | 9/2002 | Delucas et al. ................ 422/99 |
| 6,513,675 B1 | 2/2003 | Brown et al. ................. 220/608 |
| 6,517,782 B1 | 2/2003 | Horner et al. .............. 422/102 |
| 6,517,783 B2 | 2/2003 | Horner et al. .............. 422/102 |
| 6,534,015 B1 | 3/2003 | Viot et al. ................... 422/102 |
| 2003/0017084 A1 | 1/2003 | Dale et al. .................. 422/104 |

\* cited by examiner

STACKABLE ALIQUOT VESSEL ARRAY

FIELD OF THE INVENTION

The present invention relates to a method and apparatus for automatically processing a patient's biological fluids such as urine, blood serum, plasma, cerebrospinal fluid and the like. In particular, the present invention provides a stackable vessel for containing a plurality of liquid aliquot portions of patient samples in individual test wells.

BACKGROUND OF THE INVENTION

Various types of tests related to patient diagnosis and therapy can be performed by analysis assays of a sample of a patient's infections, bodily fluids or abscesses for an analyte of interest. Such patient samples are typically liquids placed in sample vials, are extracted from the vials, combined with various reagents in special reaction vessels or tubes, incubated, and analyzed to aid in treatment of the patient. In a typical clinical chemical analysis, one or two assay reagents are added at separate times to a liquid sample having a known concentration, the sample-reagent combination is mixed and incubated. Interrogating measurements, turbidimetric or fluorometric or absorption readings or the like, are made to ascertain end-point or rate values from which an amount of analyte may be determined, using well-known calibration techniques.

Although various known clinical analyzers for chemical, immunochemical and biological testing of samples are available, analytical clinical technology is challenged by increasing needs for improved levels of analysis. Automated clinical analyzers improve operating efficiency by providing results more rapidly while minimizing operator or technician error. However, due to increasing demands on clinical laboratories regarding assay throughput, new assays for additional analytes, accuracy of analytical results, and low reagent consumption, there continues to be a need for improvements in the overall performance of automated clinical analyzers. In particular, the efficiency of patient sample handling continually needs to be increased, regardless of the assay to be performed.

An important contributor to maintaining a high efficiency in throughput of patient samples is the ability to quickly and securely introduce a plurality of samples to the sample testing portion of an analyzer. Patient samples are typically held in a container such as a sample cup, a primary tube, or any other suitable container and may be open at its top or closed with a stopper or lid or the like at its top. To increase handling efficiency, the containers may then be placed into a sample rack adapted to support multiple sample containers generally in an upright orientation.

The sample rack is usually placed by an operator in an input portion of the analyzer and then moved automatically moved by the analyzer to a location where a portion of the liquid patient sample, hereinafter described as a aliquot, is extracted, usually by aspiration using a hollow, needle like probe from the sample container for testing in the analyzer. Afterwards, the aliquot may be dispensed directly into a sample test vessel or into an interim aliquot vessel prior to a later transfer into a sample test vessel.

In analyzers designed for high assay throughput numbers, efficiently handling a large number of samples introduces a number of special challenges due to simultaneous desires to maintain a relatively small analyzer footprint, maintain sample aliquots on-board the analyzer for potential re-testings, eliminate concerns for cross-contamination when reusing sample vessels, while at the same time minimizing costs associated with disposable sample vessels, etc.

It is therefore desirable to provide an aliquot vessel of small physical size, of low cost and with features permitting it to be reliably handled by automated devices. It is particularly desirable that such an aliquot vessel be able to be transported in a one-dimension linear plane on-board an analyzer so as to eliminate the necessity and expense of two-directional handling means. It is further desirable that such an aliquot vessel be capable of easily being loaded by an operator onto an analyzer, ideally being loaded from multiple vessel put-ups. It is even further desirable that such an aliquot vessel comprise a plurality of individual aliquot wells so that a single aliquot vessel accommodate a large number of different samples, for example in an array of aliquot vessels.

U.S. Pat. No. 6,190,617 provides for a test sample container including an upper skirt and a body having a reservoir for receipt of the test sample. The segment includes a base, a frame, and a handle. The frame has a shelf for which the upper skirt of the test sample container rests on, and has openings for receipt of the body of the sample container. The carousel has a carousel trough for receipt of the base of the sample container segment, and has a plurality of alignment pins disposed in the carousel trough. The base of the sample container segment has a circular slot and an elongated slot for receiving the alignment pins and positioning the sample container segment relative to the carousel.

SUMMARY OF THE INVENTION

The present invention provides a aliquot vessel array adapted with a plurality of individual sample aliquot wells and capable of being attached one atop another in a secure stack. The sample aliquot wells are designed to minimize so-called "dead sample volume" inaccessible by typical aspiration means. A number of stacked aliquot vessel arrays may be simultaneously loaded by an operator into a elevator-like storage unit on an analyzer and dispensed in a singulated stream onto a sampling track as required by the analyzer. Handling features are designed into the aliquot vessel array to ensure safe and reliable movement between the storage unit and linear sampling tracks where sample is originally dispensed into individual wells and later aspirated therefrom for sample liquid analysis. The aliquot vessel array is typically covered with an evaporation and protection layer and further includes alignment features so that multiple aspirations may be made from single punctures through the protection layer.

BRIEF DESCRIPTION OF THE DRAWINGS

The invention will be more fully understood from the following detailed description thereof taken in connection with the accompanying drawings which form a part of this application and in which:

FIG. 7A is a sectional view of a single aliquot vessel array of the present invention;

DETAILED DESCRIPTION OF THE INVENTION

Figure 1:
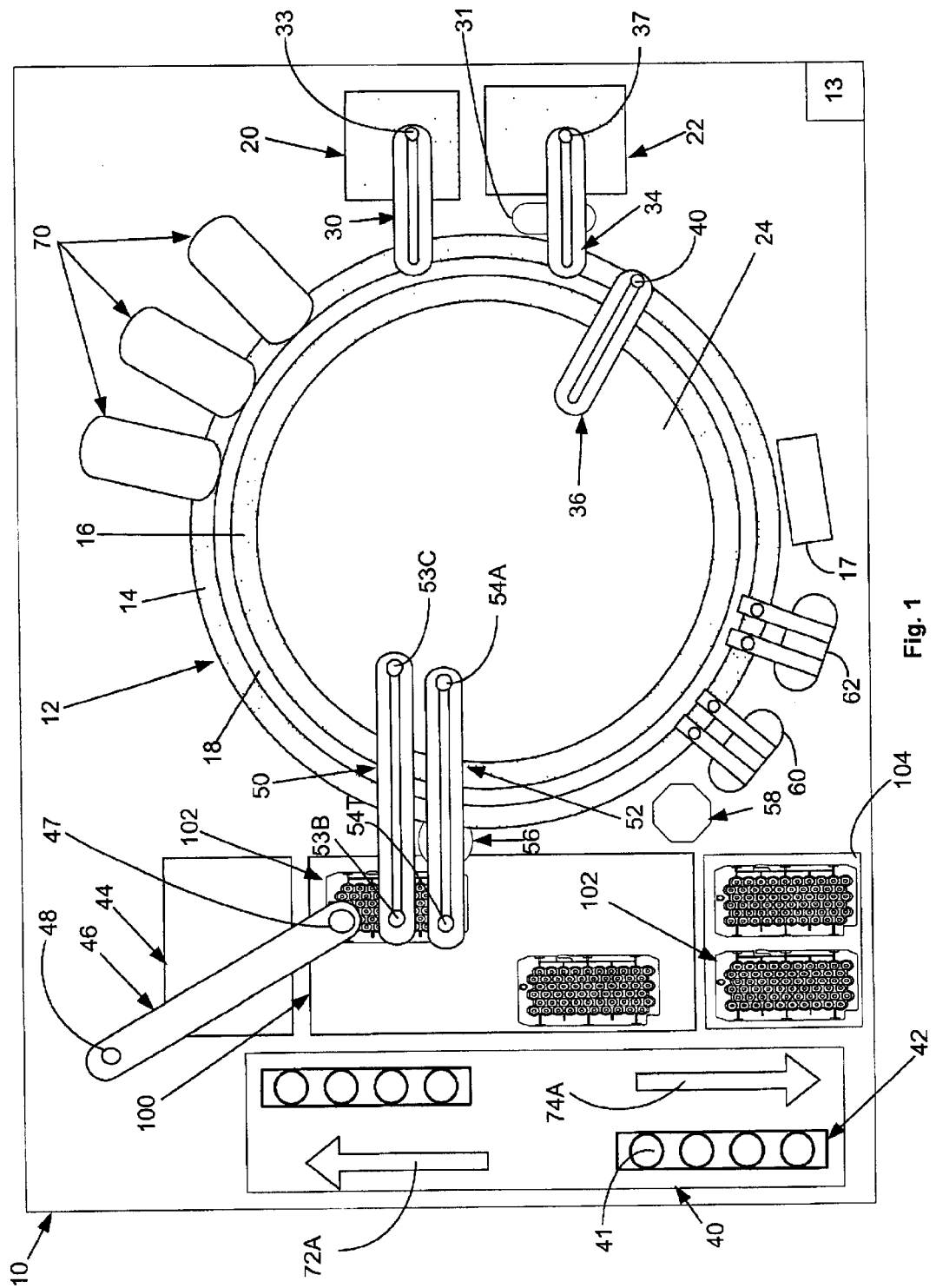
FIG. 1 is a schematic plan view of an automated analyzer in which the present invention may be used to advantage.
Figure 1A:
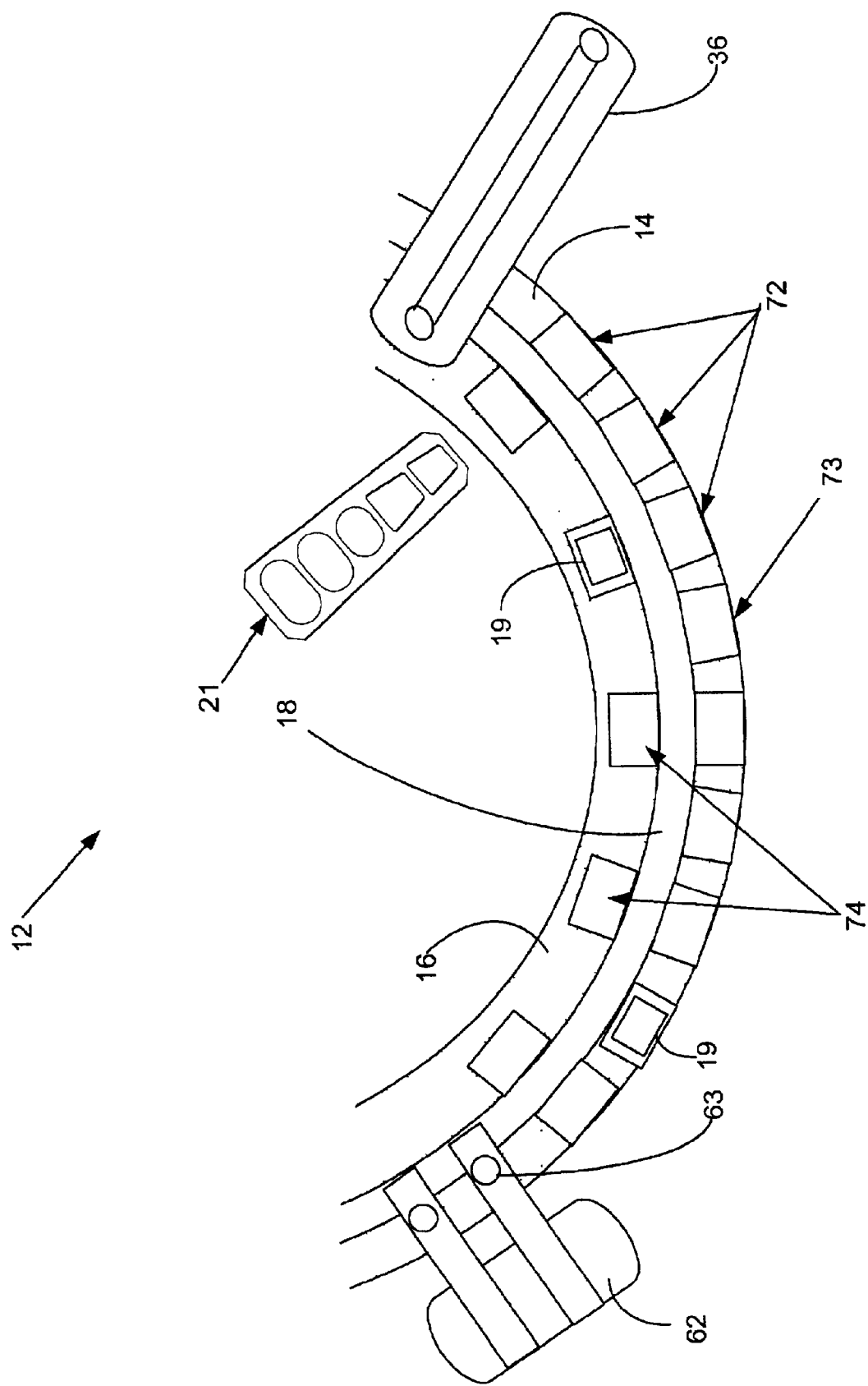
FIG. 1A is an enlarged schematic plan view of a portion of the analyzer of FIG. 1.

FIG. 1, taken with FIG. 1A, shows schematically the elements of a conventional automatic chemical analyzer 10 in which the present invention may be advantageously practiced. Analyzer 10 comprises a reaction carousel 12 supporting a outer cuvette circle 14 of cuvette ports 72 and 73 and an inner cuvette circle 16 of cuvette ports 74, the outer cuvette circle 14 and inner cuvette circle 16 being separated by a open groove 18. Cuvette ports 72, 73 and 74 are adapted to receive a plurality of reaction cuvettes 19 typically formed as small, flat walled, U-shaped containers with an open central reaction portion closed at the bottom and with an opening at the top of the cuvettes 19 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay device located proximate carousel 12 may operate on an assay mixture contained within a cuvette 19.

Three temperature-controlled reagent storage areas 20, 22 and 24 each store a plurality of reagent cartridges 21, cartridges 21, for example being a multi-compartmented reagent container like those described in U.S. Pat. No. 4,720,374, sold under the tradename FLEX® reagent cartridge by Dade Behring Inc, Deerfield, Ill., and containing reagents as necessary to perform a given assay. A selectively-opened lid (not shown) covers each of reagent storage areas 20, 22 and 24 to allow access to cartridges 21; for simplicity, only one reagent cartridge 21 is schematically illustrated in FIG. 1A as disposed beneath a cut out portion of reagent storage area 24, however similar reagent cartridges 21 are disposed within reagent storage areas 20 and 22. Shuttle means (not shown) move individual cartridges 21 to probe access ports. Storage areas 20 and 22 may be conveniently located external to the circumference of outer cuvette circle 14 and reagent storage area 24 may be conveniently located internal to the circumference of inner cuvette circle 16.

A clinical analyzer 10 like those on which the present invention may be performed has a plurality of conventional assay operation stations disposed proximate carousel 12 and at which are positioned individual computer controlled electromechanical devices, such as sensors, reagent add stations, mixing stations, and the like, as required to perform the myriad of actions required in well known clinical assays. Such devices and their operation are well known in the art and need not be described herein. See for example, U.S. Pat. Nos. 5,876,668, 5,575,976 and 5,482,861 and the references cited therein.

An indexing drive for the reaction carousel moves the reaction vessels in the constant direction a predetermined numbers of incremental steps. The length of the circumference of cuvette circle 14, the separation distance between cuvette ports 72, 73 and 74, the number of cuvette ports 72, 73 and 74, and the number of increments per indexing are selected so that any given cuvette ports 72, 73 or 74 returns to its original starting position after a fixed number of incremental steps. A number of liquid aspiration and dispense arms 30, 34, and 36 are located proximate the reagent storage areas 20, 22 and 24 and controlled by a programmed computer 13, preferably a microprocessor based central processing unit (CPU) to control all activities of analyzer 10 according to pre-programmed software, firmware, or hardware commands or circuits.

Cuvette load and unload stations 60 and 62 are positioned proximate outer cuvette carousel 14 and are conventionally adapted to load cuvettes 19 into cavities 72, 73 and 74 seen in FIG. 1A formed in both outer cuvette carousel 14 and inner carousel 16 using for example a translatable robotic clamp 63. Conventional sample processing devices, or stations 17 are positioned at selected circumferential locations about the reaction carousel 12 in order to access reaction vessels 19. Stations 17 are adapted to provide, among other processing steps, for mixing together of the sample liquid and the reagent liquid contained in a cuvette 19, for washing the sample liquid and the reagent liquid contained in a cuvette 19, and for magnetic separation of tagged magnetic particles from free tags or reagent liquid contained in a cuvette 19.

Incoming sample specimens to be tested are transported by a sample tube rack transport system 40 described in co-pending application Ser. No.: 9/992,917, assigned to the assignee of the present invention and after aspiration into aliquot vessel arrays 102, may be maintained within analyzer 10 inside an environmental chamber 44 described in co-pending application Ser. No. 09/827,045 assigned to the assignee of the present invention. Specimens are typically contained in sample containers or tubes 41 supported in sample tube racks 42 and are identified by reading bar coded indicia on sample tubes 41 using a conventional bar code reader to determine, optionally among other items, a patient's identity, the tests to be performed, if a sample aliquot is desired to be retained inside environmental chamber 44 and if so, for what period of time.

A sampling arm 46 supports a conventional liquid sampling probe 47 and is rotatably mounted so that movement of sampling arm 46 describes a line intersecting the sample tube transport system 40 and an aliquot vessel array transport system 100 adapted to transport aliquot vessel arrays 102 from an aliquot vessel array storage and handling unit 104 to a pair of conventional sample/reagent aspiration and dispense arms 50 and 52 located proximate reaction carousel 12. Sampling arm 46 is operable to aspirate liquid sample from sample tubes 41 and to dispense a liquid sample or an aliquot portion of the sample, into one or more of a plurality of wells 128 in aliquot vessel arrays 102, depending on the quantity of sample required to perform the requisite assays and to provide for a sample aliquot to be retained by analyzer 10 within environmental chamber 44. After sample has been dispensed into cuvettes, aliquot vessel array transport system 100 returns aliquot vessel arrays 102 to the aliquot vessel array storage and handling unit 104; a separate transport system (not shown, but located beneath aliquot vessel array transport system 100) removes aliquot vessel arrays 102 therefrom and deposits arrays 102 into storage compartment 44.

Various assay analyzing means 70 may be located proximate outer cuvette carousel 14 and are adapted to measure light absorbence in or emission from cuvettes 15 at various wavelengths, from which the presence of analyte in the sample liquid may be determined using well-known analytical techniques. Means 70 typically comprise conventional photometric, fluorometric or luminescent measuring devices adapted to perform an interrogating measurement at any convenient time interval during which reaction carousel 12 is stationary. Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

Analyzer 10 is controlled by computer 13 based on software written in a machine language, like that used on the Dimension® clinical chemistry analyzer sold by Dade Behring Inc, of Deerfield, Ill., and widely used by those skilled in the art of computer-based electromechanical control programming.

Figure 2:
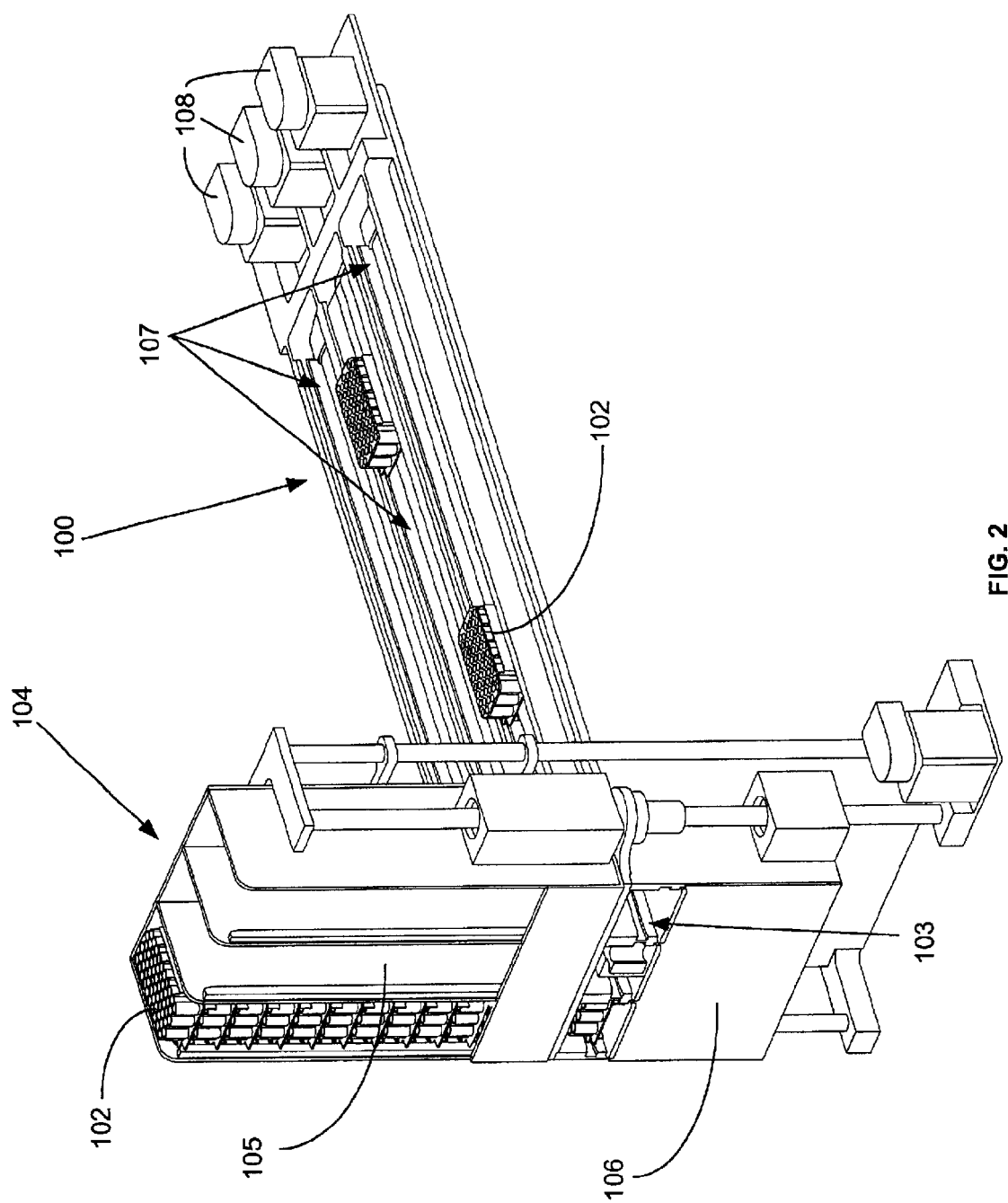
FIG. 2 is a perspective elevation view of an automated aliquot vessel array storage and handling unit integrated with a sampling track in which the present invention may be used to advantage.
Figure 3:
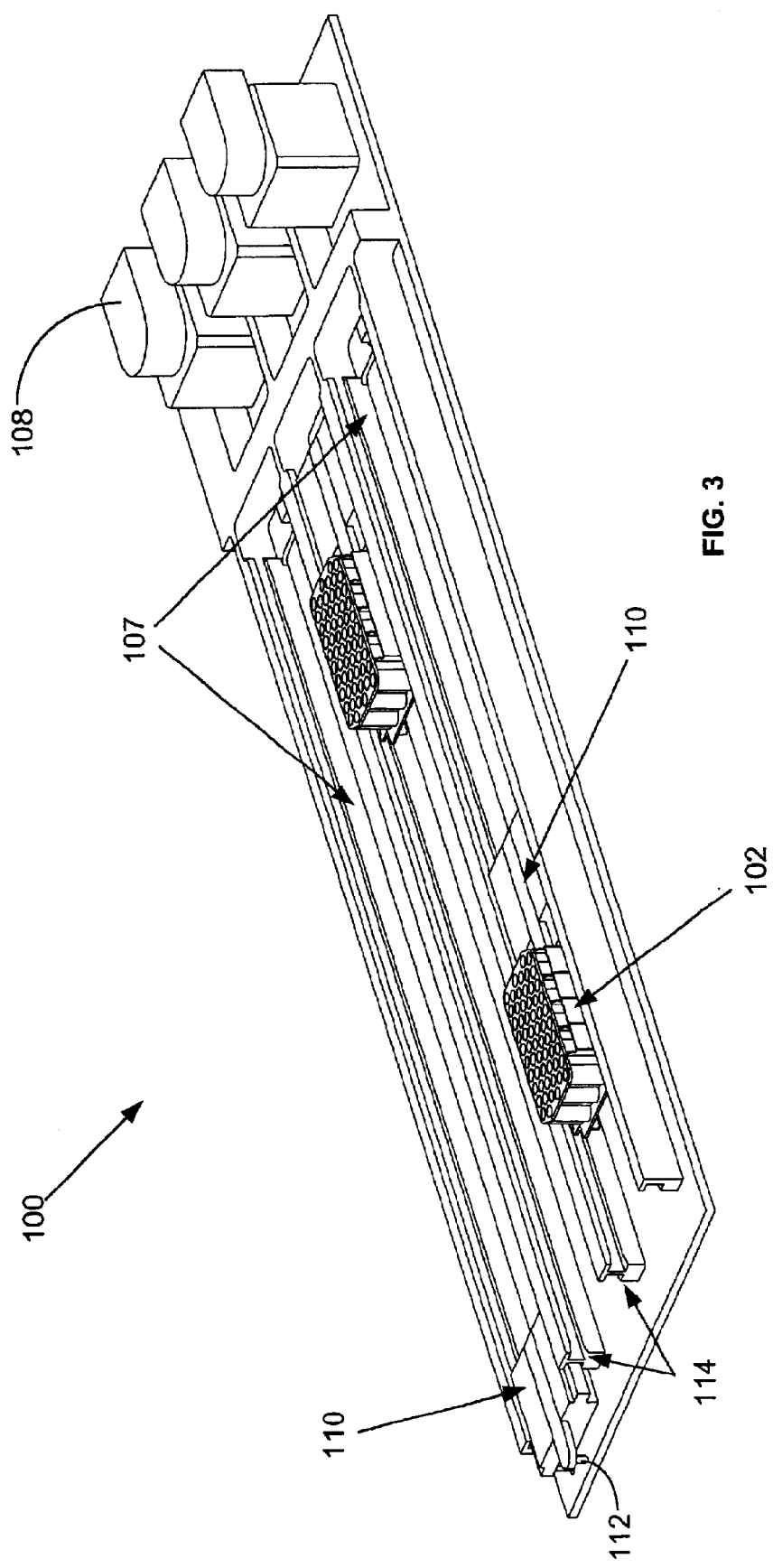
FIG. 3 is a perspective elevation view of the sampling track of FIG. 2 illustrating an entry point for aliquot vessel arrays provided by the present invention into the sampling track.

As seen in FIG. 2, automated aliquot vessel array storage and handling unit 104 is disposed proximate aliquot vessel array transport system 100 and is adapted in a manner described hereinafter so that aliquot vessel arrays 102 may be automatically transferred from a vertically translatable array elevator 106 from any of three aliquot vessel array inventory shafts 105 within aliquot vessel array storage unit 104 onto one of several pairs of parallel aligned aliquot vessel array sampling tracks 107. Aliquot vessel arrays 102 are mounted within aliquot vessel array storage unit 104 between pairs of storage tracks 103 having flared open ends 101 suitable for discharging and receiving an aliquot vessel array 102, described later in conjunction with FIG. 9. Two aliquot vessel arrays 102 are seen located between a pair of sampling tracks 107. The lengthwise positioning of an aliquot vessel array 102 between sampling tracks 107 is provided by a motor-driven dolly 110 independently moveable in either direction within a pair of sampling tracks 107, the dolly 110 being connected for example by a thread-screw or ladder chain (not shown) to an independently operable stepping motor 108 (see FIG. 3). Each dolly 110 has a protruding and downwardly projecting finger-latch 112 adapted to secure an aliquot vessel array 102 via a zero-backlash feature described later. The ends of tracks 107 opposite from motors 108 are open and as seen in FIG. 3, terminate with a set of flared open ends 114 suitable for receiving an aliquot vessel array 102, described later in conjunction with FIG. 9.

Figure 4:
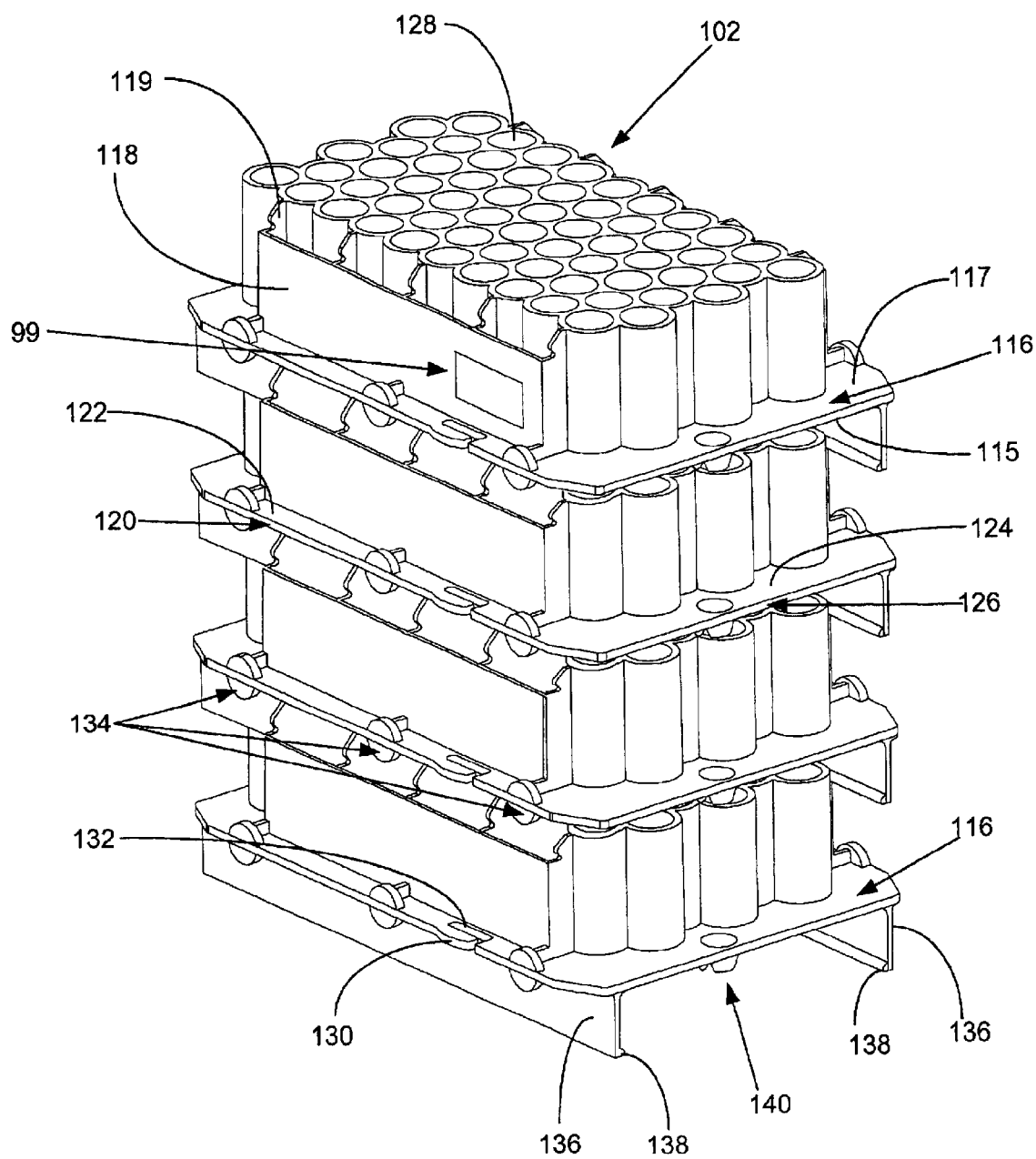
FIG. 4 is perspective elevation view of four aliquot vessel arrays of the present invention, secured together into a single stack.

FIG. 4 illustrates a number of the important features found in the aliquot vessel array 102 of the present invention. As seen therein, a number of aliquot vessel arrays 102 may be snapped together one atop another shown as a mutually aligned vertical stack of four aliquot vessel arrays 102. Each aliquot vessel array 102 comprises an orthogonal base plate 116 having a pair of upwardly extending and mutually parallel first and second side walls 118 and 119 extending lengthwise along a longer orthogonal edge 120 of the base plate 116, the side walls 118 and 119 positioned inside the outer boundary of base plate 116 and having a length shorter than the longer orthogonal edge 120 so that a longer perimeter portion 122 remains along the outermost portions of base plate 116 along the longer orthogonal edge 120 and a shorter perimeter portion 124 remains along the outermost portions of base plate 116 along a shorter front orthogonal edge 126 of the base plate 116. A shorter rear orthogonal edge 127 of the base plate 116 may be seen in the plan view of aliquot vessel array 102 in FIG. 7. An optional recessed "billboard" portion 99 may be formed in either of the first and second side walls 118 and 119 in order to frame an conventional barcode identifying indicia for the aliquot vessel array 102.

An ordered array of open wells 128 is further formed on base plate 116 extending upwardly therefrom and confined between the pair of parallel side walls 118 and 119. The parallel side walls 118 are attached to the array of open wells 128 by a number of notched side flanges 121 best seen in FIG. 6 having a notch 125 adapted to mate with a foot section 138 of a rail 136. A pair of parallel rails 136 extend approximately the full length of the longer orthogonal edges 120 of base plate 116 and depend downwardly from the lower surfaces 115 of the base plate 116 proximate the longer orthogonal edges 120.

In an exemplary embodiment, base plate 116 has dimensions about 5 cm in width and 7.5 cm in length, side walls 118 are about 3–4 cm in length centered along the longer orthogonal edge 120 of the base plate 116 and extend about 1.1 cm upwardly from base plate 116. Wells 128 are about 0.6 cm in diameter, extend about 2 cm above base plate 116 and are about 60 in number in the embodiment described. Typically, aliquot vessel arrays 102 may be formed of low cost plastic material in large quantities using well known plastic molding operations and may be disposed after a single use without significantly adding to the expense of operation of analyzer 10; furthermore, the use of disposable aliquot vessel arrays 102 eliminates the possibility of sample cross-contamination created when sample aliquot holders are washed and re-used with different patient samples.

Figure 5:
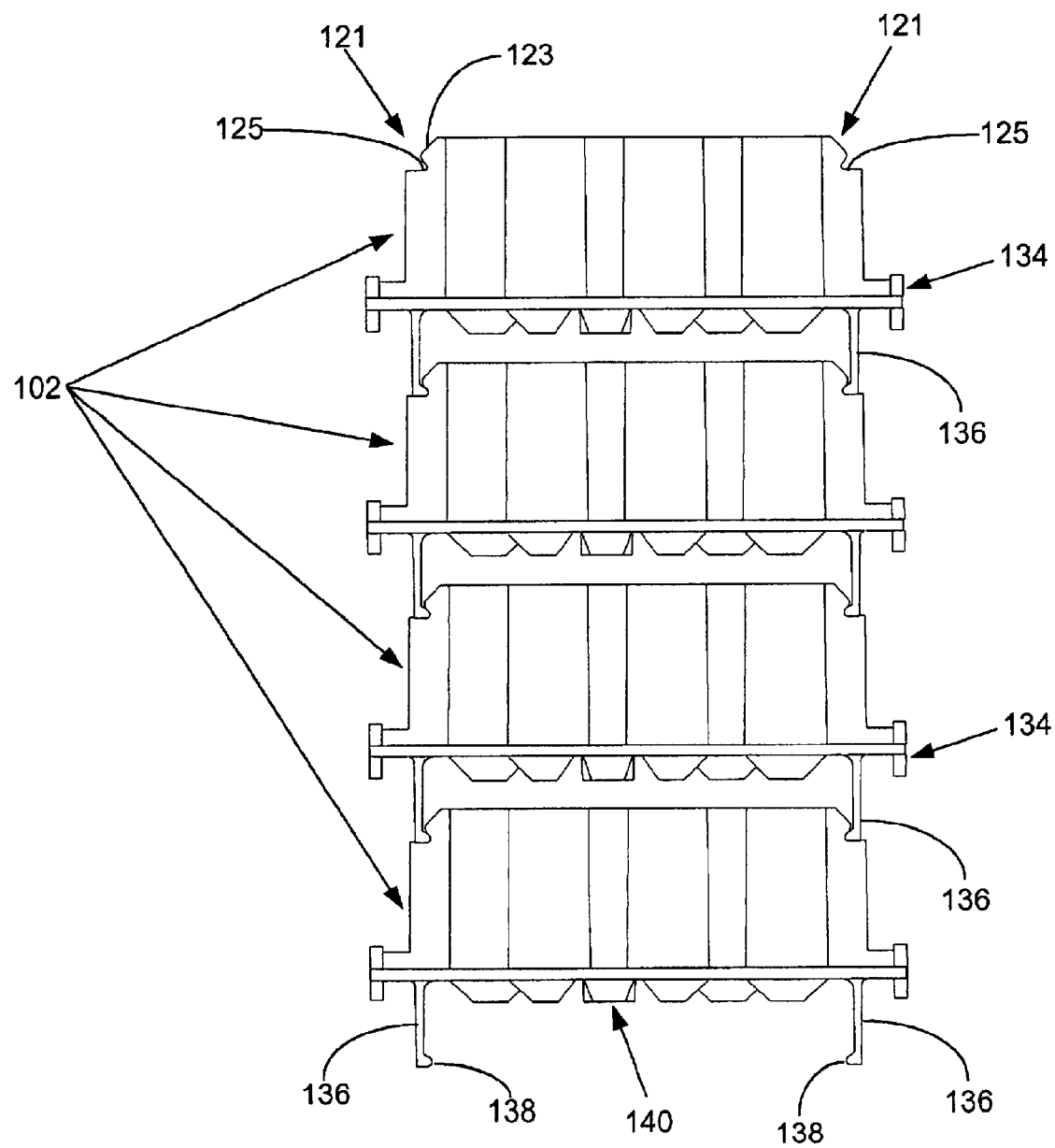
FIG. 5 is front elevation view of the single stack of four aliquot vessel arrays of the present invention seen in FIG. 4.
Figure 6:
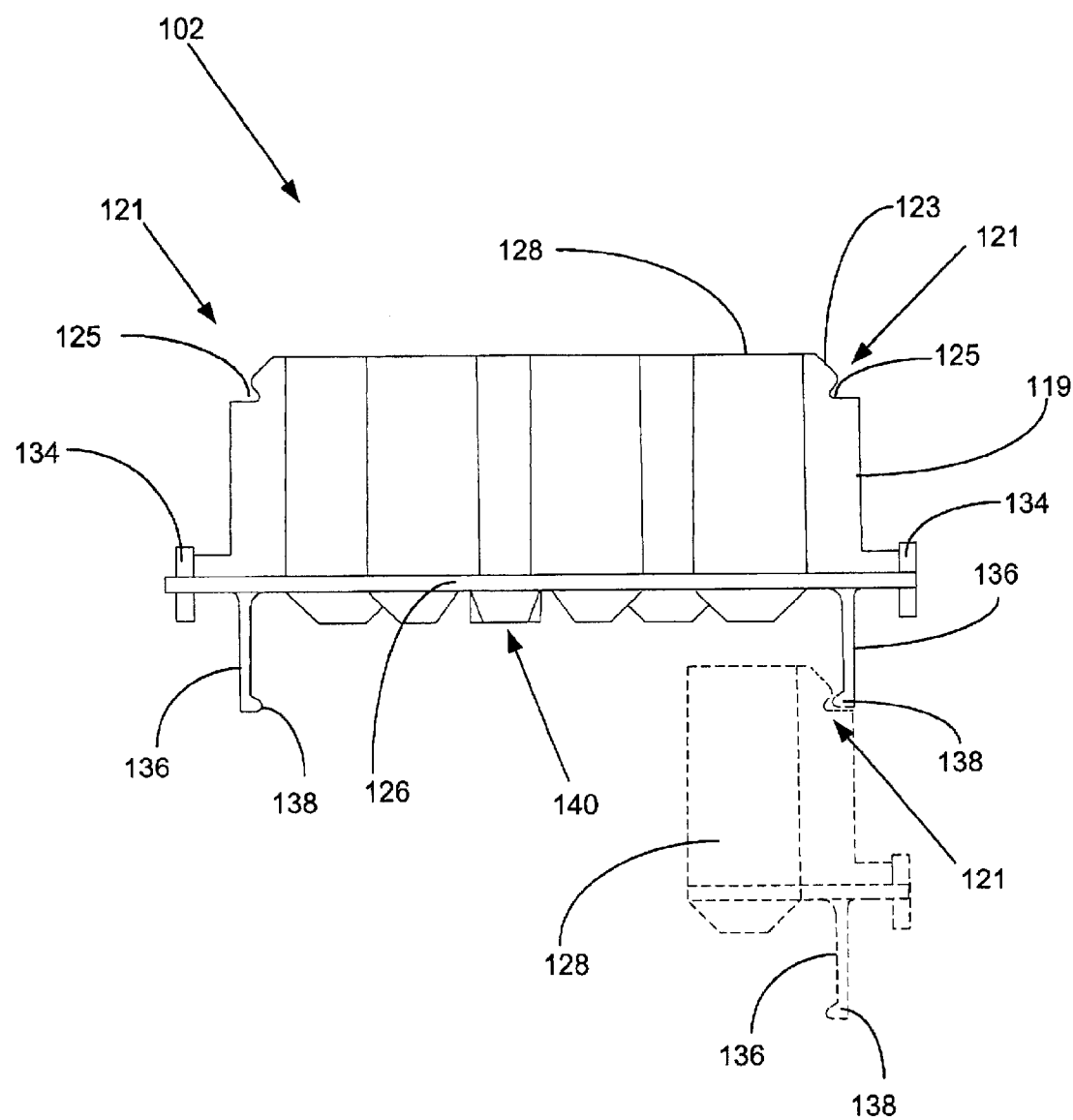
FIG. 6 is a is front elevation view of a single aliquot vessel array of the present invention.

FIGS. 4 and 5 shows how a number of aliquot vessel arrays 102 may be stacked atop one another by mating the notched side flanges 121 with the foot sections 138 of parallel rails 136 along the longer orthogonal edges 120 of base plate 116. Notched side flanges 121 include an inclined guide 123 leading to the notch 125 of notched side flanges 121 so that as a second aliquot vessel array 102 is pushed downwards over a first aliquot vessel array 102, the parallel rails 136 of the second aliquot vessel array 102 slide down, slightly outwards and then over inclined guides 123 so that the foot sections 138 of the rails 136 snap into notches 125, thereby securing the pair of aliquot vessel arrays 102 together. Additional aliquot vessel arrays 102 may be similarly pushed downwards over and snapped atop the pair of aliquot vessel arrays 102 so that a stack of multiple aliquot vessel arrays 102 may easily be formed. FIG. 5 in particular shows four aliquot vessel arrays 102 snapped atop one another into a single stack. The purpose of this snap-together feature of the aliquot vessel array 102 of the present invention is to facilitate the loading by an operator of a number of aliquot vessel arrays 102 into the aliquot vessel array storage chutes 105 of vessel array storage and handling unit 104 as seen in FIG. 2. FIG. 6 is an enlarged front elevation view showing how the foot section 138 of rail 136 of the second aliquot vessel array 102 snaps over and engages the notch 125 of a notched side flange 121 of a "phantom" aliquot vessel array 102 (shown in dashed lines).

Figure 7:
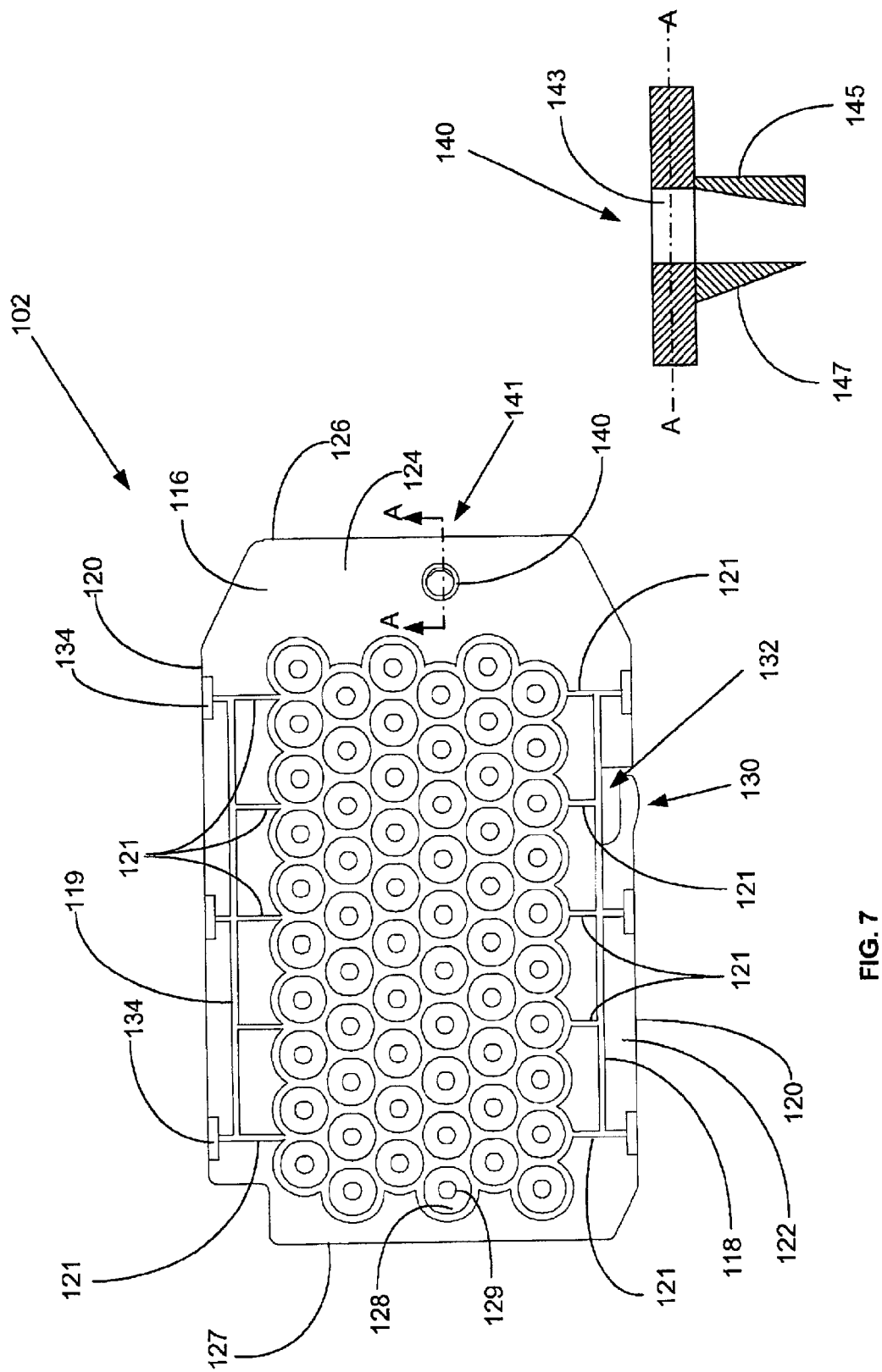
FIG. 7 is a plan view of a single aliquot vessel array of the present invention.

FIG. 7 is a plan view of the aliquot vessel array 102 of the present invention showing the spatial relationships between parallel first and second side walls 118 and 119 extending lengthwise along the longer orthogonal edges 120 of the base plate 116. The ordered array of open wells 128 is between the pair of parallel side walls 118 and 119, separated therefrom by notched side flanges 121. Front orthogonal edge 126 and rear orthogonal edge 127 of the base plate 116 are further seen to be formed mutually parallel to one another with zero-backlash hitch 140 described hereinafter formed in the central region 141 of the front shorter perimeter portion 124 between the array of open wells 128 and front orthogonal edge 126. As better seen in FIG. 8A, each of the open wells 128 has a cylindrical shape depending downwardly from an open top and is closed at the lowermost end by conical shaped walls 128W leading to a flat circular bottom 128B. Such conical shaped walls 128W and flat circular bottom 128B have been found to be effective in minimizing liquid remaining in wells 128 during sample aspiration process.

Another important feature of the aliquot vessel array 102 of the present invention is the zero-backlash hitch 140 formed in the central region 141 of the front shorter perimeter portion 124 between the shorter orthogonal edge 126 and the array of open wells 128. Sectional line A—A in FIG. 7A is enlarged to show details of zero-backlash hitch 140 comprising an opening 143 in base plate 116 and a pair of semi-circular sleeves extending downwardly, a frontal sleeve 145 formed to slant backwards from the front of aliquot vessel array 102 towards a rear sleeve 147 formed generally perpendicularly to base plate 116. The pair of semi-circular sleeves are spaced apart a distance so that finger-latch 112 of dolly 110 may be inserted between the frontal sleeve 145 and rear sleeve 147 in such a manner that the backwards slanting frontal sleeve 145 biases finger-latch 112 against rear sleeve 147, thereby ensuring that aliquot vessel array 102 may be accurately positioned within track 107 by a ladder-chain, for example, securing dolly 110 to motor 108. The backwards slanting frontal sleeve 145 thereby provides zero-backlash locations to aliquot vessel array 102 throughout a repeated number of movements in both directions within track 107. As explained later, aliquot vessel array 102 is repeatedly moved to a single sampling location in track 107 whereat multiple aliquots of sample are aspirated from wells 128, wells 128 being environmentally sealed with a conventional laminate covering (not shown) and punctured by an aspiration needle. It is important that aliquot vessel array 102 be accurately positioned within track 107 by zero-backlash hitch 140 so that only a single aspiration puncture is made in the laminate covering during multiple sample aspirations thereby minimizing sample evaporation losses during subsequent storage of the aliquot vessel array 102.

Figure 8:
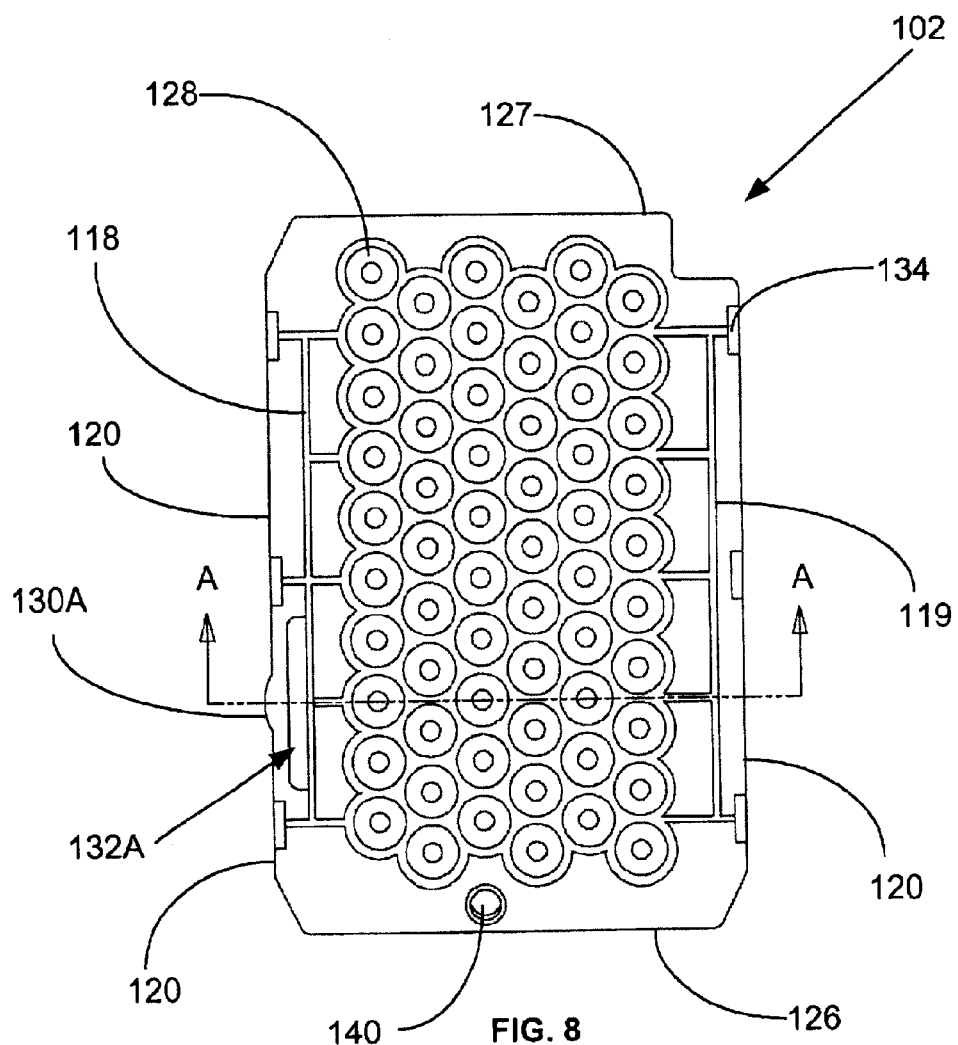
FIG. 8 is an plan view of an alternate embodiment of the aliquot vessel array of the present invention.

An important feature of aliquot vessel array 102 seen in FIG. 7 is a securing finger 130 formed in the longer perimeter portion 122 of the base plate 116 along a single longer orthogonal edge 120 proximate first parallel side wall 118 and located midway between the frontmost two of three transfer hubs 134. Securing finger 130 protrudes slightly outwards from longer orthogonal edge 120 and separated from longer perimeter portion 122 by means of a notch 132 cut within longer perimeter portion 122 between first side wall 118 and longer orthogonal edge 120 of the base plate 116. FIG. 8 is an alternate embodiment of the aliquot vessel array of the present invention in which a securing bulge 130A is also formed in the longer perimeter portion 122 of the base plate 116 and may conveniently be located midway between the frontmost two of three transfer hubs 134. Securing bulge 130A protrudes slightly outwards from longer orthogonal edge 120 and is separated from longer perimeter portion 122 by means of an elongate opening 132A cut within longer perimeter portion 122 between first side wall 118 and longer orthogonal edge 120 of the base plate 116. Both securing finger 130 and securing bulge 130A act to securely retain aliquot vessel arrays 102 within array elevator 106.

Figure 8A:
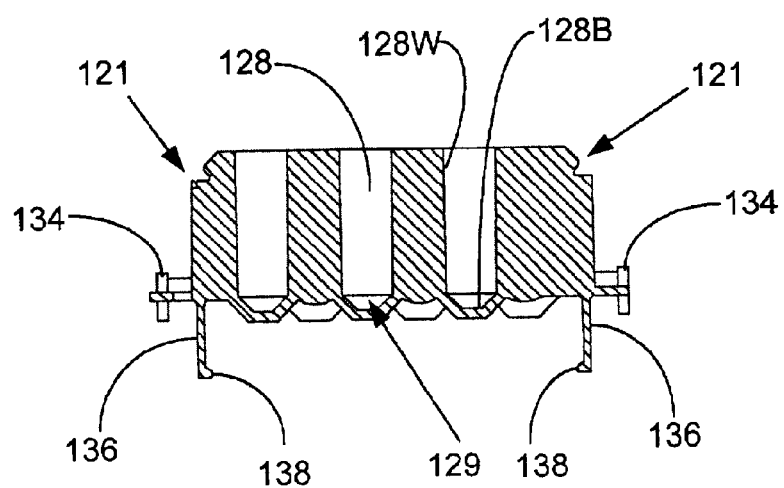
FIG. 8A is a sectional view of the aliquot vessel array of the present invention; and, FIGS. 9A–E are schematic views of the transferring of a single aliquot vessel array of the present invention from the storage and handling unit of FIG. 2 to the sampling track of FIG. 3.

In addition, three transfer hubs 134, best seen in FIGS. 4 and 8A, are formed fully within and equally spaced along the longer perimeter portion 122 between the first side wall 118 and longer orthogonal edge 120, transfer hubs 134 having a solid cylindrical shape axially aligned with the plane of base plate 116 so that approximately equal portions of the transfer hubs 132 extend above and below the base plate upper surface 117 and base plate lower surface 115 of base plate 116. FIGS. 9A–E illustrate the utility of the three transfer hubs 134 in transferring a aliquot vessel array 102 from within an array elevator 106 to aliquot vessel array transport system 100 where sample/reagent aspiration and dispense arms 50 and 52 aspirate liquid sample from sample tubes 41 and dispense a sample aliquot into one or more of a plurality of wells 128 in aliquot vessel arrays 102. As described before, aliquot vessel arrays 102 supported on storage tracks 103 within array elevators 106 may be vertically positioned by array elevator 106 into approximate alignment with a pair of array sampling tracks 107 so that an aliquot vessel array 102 may be automatically and reliably transferred therebetween. The expense of precisely machined parts and use of multiple sensors that may otherwise be required to ensure exact alignment between the storage tracks 103 and sampling tracks 107 may be avoided by means of the three transfer hubs 134, as seen in FIGS. 9A–E.

Figure 9A:
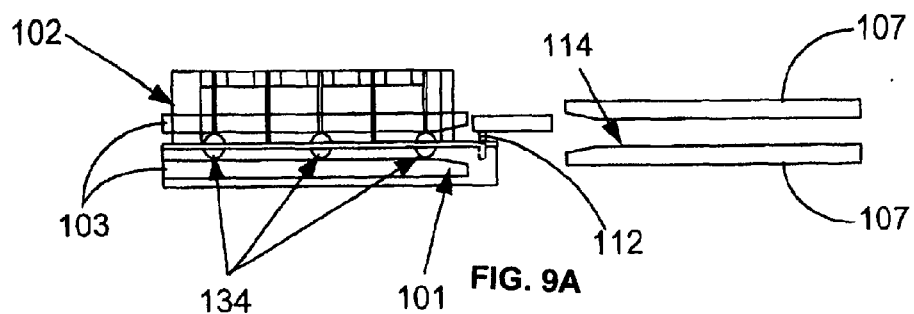
Figure 9B:
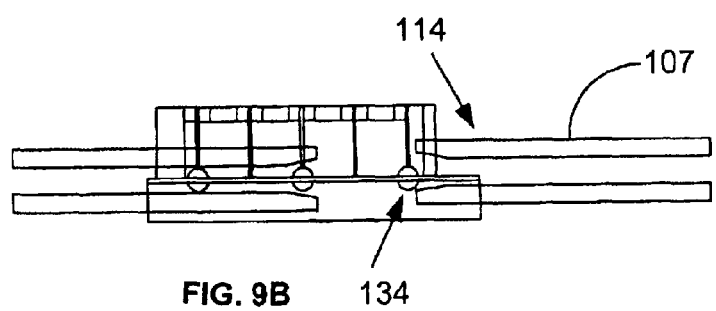

FIG. 9A schematically shows an aliquot vessel array 102 supported on storage tracks 103 of vessel array elevator 106 prior to removal therefrom and engaged by finger-latch 112 inserted into zero-backlash hitch 140. (Finger-latch 112 and hitch 140 are not shown in the remainder of FIG. 9 for purposes of simplicity.) Storage tracks 103 and sampling tracks 107 are purposefully shown as being misaligned in order to illustrate the function of the three transfer hubs 134 in FIGS. 9B–E. FIG. 9B shows aliquot vessel array 102 moved "rightwards" and in a position approaching the misaligned sampling tracks 107; importantly, aliquot vessel array 102 is still constrained and secured by two transfer hubs 134 engaged within tracks 103.

Figure 9C:
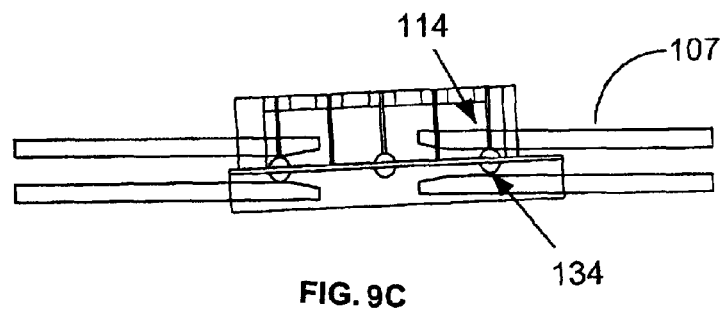

FIG. 9C shows the first of three transfer hubs 134 of aliquot vessel array 102 as ramped upwards and engaged within the flared open ends 114 of sampling tracks 107. Because the aliquot vessel array 102 is being supported by circular transfer hubs 134, the aliquot vessel array 102 is free to tilt upwards or downwards with its "front end" engaged within sampling tracks 107 and its "rear end" engaged within misaligned sampling tracks 107.

Figure 9D:
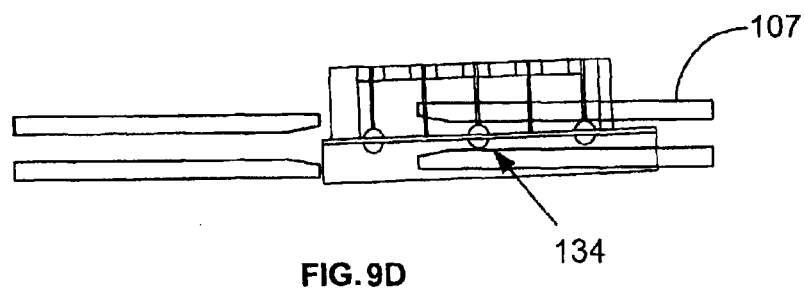
Figure 9E:
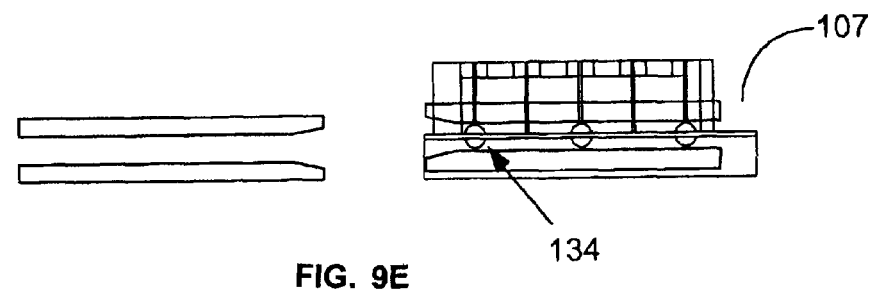

As the finger-latch 112 continues to pull the aliquot vessel array 102 to the right, and as seen in FIG. 9D, the second of three transfer hubs 134 of aliquot vessel array 102 is ramped upwards and similarly engaged within the flared open ends 114 of sampling tracks 107. The process continues until aliquot vessel array 102 is fully engaged within sampling tracks 107. When employing the aliquot vessel array 102 of the present invention and having these three transfer hubs 134, it is important to adjust the opening between the storage tracks 103 and sampling tracks 107 so that at all times during the transfer process, at least two of the three transfer hubs 134 are fully engaged within the storage tracks 103 or sampling tracks 107, as seen in FIGS. 9A, 9B, 9D and 9E, or that a single transfer hub 134 is fully engaged within both of the storage tracks 103 and sampling tracks 107, FIG. 9C.

Advantageously, foot sections 138 and transfer hubs 134 both enable aliquot vessel arrays 102 to be transportable in a single one-dimension linear plane on-board an analyzer so as to eliminate the necessity and expense of two-directional handling means. In particular, aliquot vessel arrays 102 are linearly removal from vessel array elevator 106 by finger-latch 112 sliding the notched side flanges 121 of a first aliquot vessel array 102 outwards from engagement with the foot sections 138 of a second aliquot vessel array 102 stacked atop first aliquot vessel array 102. Aliquot vessel arrays 102 are also linearly moveable between storage tracks 103 or sampling tracks 107 by means of transfer hubs 134 as described in FIGS. 9A–9E.

In operation of the analyzer of FIG. 1, an operator simply removes a stack of 5 to 10 aliquot vessel arrays 102 of the present invention from a shipping container and secured together by means of the notched side flanges 121 mated with foot sections 138 of a rail 136 of a next adjacent aliquot vessel arrays 102, and places them into any of three aliquot vessel array inventory shafts 105 within aliquot vessel array storage and handling unit 104. Array elevator 106 is controlled by CPU 13 to automatically transfer a singulated stream of aliquot vessel arrays 102 by means of zero-backlash hitch 140 coupled with finger-latch 112 of dolly 110 into one of several pairs of parallel aligned aliquot vessel array sampling tracks 107, as seen in FIG. 9. Each aliquot vessel array 102 is moved by motor 108 to a single sampling location in track 107 whereat multiple aliquots of liquid sample are aspirated from wells 128 of aliquot vessel arrays 102 by means of a single aspiration puncture in the laminate covering of the aliquot vessel array 102. After multiple aspirations have removed sufficient liquid sample to perform all assays requested by CPU 13, aliquot vessel arrays 102 are returned to storage and handling unit 104 and may be inventoried within analyzer 10 inside an environmental chamber 44.

It will be appreciated by those skilled in that art that a number of design variations may be made in the above and still achieve the essence of the present invention. For these reasons, the present invention is not limited to those embodiments precisely shown and described in the specification but only by the following claims.

We claim:

1. An aliquot vessel array for containing a plurality of liquid patient samples in test wells, said array comprising:
   a base plate having an upper surface and a lower surface with a pair of mutually parallel side walls extending upwardly from the upper surface, the base plate having also having a zero-backlash hitch formed therein;
   a pair of parallel rails depending downwardly from the base plate, each parallel rail having a foot section at its lower extremity; and,
   an array of open test wells formed on the base plate extending upwardly therefrom and confined between the pair of parallel side walls,
   wherein the parallel side walls are attached to the array of open wells by a number of notched side flanges having a notch adapted to mate with the foot section of a rail.

2. The array of claim 1 wherein the base plate is defined by mutually parallel longer edges perpendicular to mutually parallel shorter edges, the mutually parallel side walls extending lengthwise along the longer edges and being positioned inside the outer boundary of the base plate, the side walls having a length shorter than the longer edges so that a longer perimeter portion remains along the outermost portions of base plate along the longer edges and a shorter perimeter portion remains along the outermost portions of base plate along the shorter edges.

3. The array of claim 2 wherein the a zero-backlash hitch is formed in the a shorter perimeter portion of the base plate.

4. The array of claim 2 wherein a securing bulge is formed in a longer perimeter portion of the base plate.

5. The array of claim 2 wherein a securing finger is formed in a longer perimeter portion of the base plate.

6. The array of claim 2 wherein a number of transfer hubs are formed in each of the longer perimeter portions of the base plate between a side wall and a longer edge, the transfer hubs having a cylindrical shape axially aligned with the plane of the base plate so that approximately equal portions of the transfer hubs extend above the upper and lower surfaces of the base plate.

7. The array of claim 1 wherein each of the test wells has a cylindrical shape depending downwardly from an open top and is closed at the lowermost end by conical shaped walls leading to a flat circular bottom so as to minimize liquid remaining in wells during a sample aspiration process.

8. The array of claim 1 wherein the zero-backlash hitch comprises an opening in the base plate and a pair of semi-circular sleeves extending downwardly therefrom, one sleeve formed to slant backwards from the front of the array towards the other sleeve formed generally perpendicularly to the base plate, the pair of semi-circular sleeves being spaced apart a predetermined distance.

9. The array of claim 4 wherein the securing bulge protrudes slightly outwards from the longer edge of the base plate and an elongate opening is formed within the longer perimeter portion between the side wall and the longer edge of the base plate.

10. The array of claim 5 wherein the securing finger protrudes slightly outwards from the longer edge of the base plate and is separated from the longer perimeter portion by a notch formed within longer perimeter portion between side wall and longer edge.

11. The array of claim 1 further comprising a recessed portion formed in a side wall to frame an identifying indicia.

12. The array of claim 1 wherein the notched side flanges comprise an inclined guide leading to the notch so that the parallel rail of another aliquot vessel array slides over the inclined guide and snap the foot sections of the rails snap into the notches, thereby to secure the pair of aliquot vessel arrays together.

13. A multiple number of the aliquot vessel arrays of claim 1 stacked atop one another by mating the notched side flanges of one aliquot vessel array with the foot sections of parallel rails of a next adjacent aliquot vessel array.

* * * * *